United States Patent [19]

Shalaby et al.

[11] Patent Number: 5,422,068
[45] Date of Patent: Jun. 6, 1995

[54] RADIOCHEMICAL STERILIZATION

[76] Inventors: Shalaby W. Shalaby, 68 Prospect Ave., Guilford, Conn. 06437; Charles L. Linden, Jr., 5507 Johnson Ave., Bethesda, Md. 20817

[21] Appl. No.: 177,872
[22] Filed: Jan. 5, 1994
[51] Int. Cl.$^6$ .......................... A61L 2/00; A61L 2/08
[52] U.S. Cl. .................... 422/22; 250/455.11; 422/23; 422/28; 422/29; 422/30; 422/32; 422/36; 422/186; 422/186.05
[58] Field of Search ............... 422/22, 23, 120, 28, 422/29, 30, 32, 36, 38, 186, 186.05; 250/455.11; 206/438, 439

[56] References Cited

U.S. PATENT DOCUMENTS

| 2,831,749 | 4/1958 | Marinaro et al. | |
|---|---|---|---|
| 3,117,832 | 1/1964 | Thomas | 422/29 X |
| 3,310,364 | 3/1967 | Rijssenbeek | 422/36 |
| 3,494,726 | 2/1970 | Barasch | 422/29 |
| 3,591,476 | 7/1971 | Battaerd | |
| 3,594,293 | 7/1971 | Marens | |
| 3,630,348 | 12/1971 | Benson et al. | 422/36 X |
| 3,697,222 | 10/1972 | Sierra | 422/20 |
| 3,912,450 | 10/1975 | Boucher | 422/20 |
| 3,929,662 | 12/1975 | Boucher | |
| 3,983,252 | 9/1976 | Buchalter | 422/36 |
| 4,050,576 | 9/1977 | Williams et al. | 422/36 X |
| 4,128,397 | 12/1978 | Lunch | 422/29 |
| 4,169,123 | 9/1979 | Moore et al. | 422/32 |
| 4,182,663 | 1/1980 | Vaseen | 422/29 X |
| 4,207,286 | 6/1980 | Boucher | 422/28 X |
| 4,214,962 | 7/1980 | Pincon | 422/186.12 X |
| 4,374,814 | 2/1983 | Gaylord | 422/36 X |
| 4,400,357 | 8/1983 | Hohmann | 422/297 |
| 4,448,750 | 5/1984 | Fuesting | 422/20 |
| 4,569,736 | 2/1986 | Kosegaki et al. | 422/22 X |
| 4,717,544 | 1/1988 | Calcaterra et al. | 422/29 X |
| 4,839,004 | 6/1989 | Castellini | 422/22 |
| 4,865,602 | 9/1989 | Smestad et al. | 422/22 X |
| 4,874,489 | 10/1989 | Callerame | 423/477 X |
| 4,896,768 | 1/1990 | Anderson | 422/22 X |
| 4,931,261 | 6/1990 | Jacob | 422/22 |
| 5,011,600 | 4/1991 | Arena | 422/23 X |
| 5,019,344 | 5/1991 | Kutner et al. | 422/21 |
| 5,019,359 | 5/1991 | Kutner et al. | 422/294 |
| 5,135,714 | 8/1992 | Wang | 422/34 X |
| 5,141,722 | 8/1992 | Nagashima | 422/292 |
| 5,213,759 | 5/1993 | Castberg et al. | 422/24 |

FOREIGN PATENT DOCUMENTS

| 2081231 | 12/1971 | France . | |
|---|---|---|---|
| 5116354 | 6/1980 | Japan . | |
| 2109566 | 4/1990 | Japan | 422/29 |
| 387881 | 5/1965 | Switzerland . | |
| 2066076 | 7/1981 | United Kingdom . | |

OTHER PUBLICATIONS

A Bacteriological Survey of Sanitary Dressings, and Development of an Effective Means for their Disposal, C. M. Lucas, et al., J. Hyg. Camb., 1980, Cambridge University Press.

Surface-Decontaminating Action of Glutaraldehyde in the Gas-Aerosol Phase, A. Bovallius, et al. Applied and Environmental Microbiology, Aug. 1977, pp. 129–134, vol. 34, No. 2, Copyright 1977 American Society for Microbiology.

Primary Examiner—Robert J. Warden
Assistant Examiner—Krisanne M. Thornton

[57] ABSTRACT

Radiochemical sterilization is accomplished by exposing a sterilant gas releasing substrate to an effective gas releasing amount of ionizing radiation and contacting an object to be sterilized with the released sterilant gas. Objects to be sterilized may be subjected to a combination of ionizing radiation and gas sterilant which is released by the ionizing radiation.

21 Claims, No Drawings

RADIOCHEMICAL STERILIZATION

BACKGROUND OF THE INVENTION

1. Field of the Invention

The present invention relates to sterilization of articles. More particularly, the present invention relates to sterilization by irradiation and radiolyric decomposition of substrates and consequent release of a sterilant gas.

2. Description of Related Art

Sterilization and disinfection are important procedures used for the reduction or elimination of disease causing organisms or agents. Sterilization and disinfection are very important, e.g., in sanitation or medicine to reduce or prevent the spread of infections and the like.

Traditional methods of sterilization include the use of steam, dry heat, chemicals, and radiation. Steam and dry heat, while effective in certain cases, require high temperatures which may not be suitable for all products which are to be used or reused. Chemicals which are used for sterilization include gases such as ethylene oxide, propylene oxide, formaldehyde, glutaraldehyde, methyl bromide, ozone and propriolactone. Chemical sterilants are useful on materials which may be sensitive to the effects of heat or moisture.

A popular gas sterilant is ethylene oxide which, unfortunately, is potentially explosive and is primarily a surface sterilant. Formaldehyde has also been used but drawbacks include instability of stock solutions, toxicity, the need for heat and humidity in certain instances, explosiveness at typical gas phase concentrations, and a substantial lack of penetration into the object being sterilized.

Radiation sterilization includes the use of ultraviolet rays, electron beams, x-rays, gamma rays, and to a limited extent, gas plasma and microwave radiation. Some radiation sterilization is considered to be a volume sterilant, i.e., capable of good penetration and sterilizing throughout a volume with substantially equal results. However, ultraviolet radiation and gas plasma are predominantly surface sterilants without substantial penetration. Moreover, most forms of radiation are known to degrade certain polymers and may be detrimental to products incorporating those polymers.

Attempts have been made to combine certain of the above sterilants. For example, U.S. Pat. No. 3,117,832 describes simultaneous use of toxic gases such as ethylene oxide or propylene oxide, ozone and ultraviolet rays. Swiss Patent No. 387,881 describes sterilization by the simultaneous action of vapors of methanogen, trioxymethylene, formaldehyde, or aldylene, with ozone and ultraviolet rays. The vapors are released into the chamber by heating. Japanese Kokai 55-116354 describes artificial kidney sterilization with an aqueous solution of formaldehyde in combination with gamma irradiation and avoidance of gas bubbles.

Generation of a gas sterilant or disinfectant has been an important field of study. For example, a chlorine dioxide gas disinfectant may be generated by subjecting a solid chlorite to ultraviolet radiation as is described in U.S. Pat. No. 4,874,489. Sustained release of a gaseous sterilant is described in U.S. Pat. No. 4,717,544 where solid polymeric aldehydes are thermally depolymerized to afford gas phase monomers. U.S. Pat. Nos. 4,400,357, 5,019,344 and 5,019,359 describe generation of gas sterilants by heating with microwave radiation. The '344 and '359 patents involve the combined effect of microwave radiation and the gas sterilant on the object to be sterilized. Packages containing an object to be sterilized and a sterilant which is heat releasably bonded to a substrate are described in U.S. Pat. No. 3,494,726. U.S. Pat. No. 4,050,576 describes subjecting a polyacetal to high energy irradiation without effecting depolymerization, which as a result, can then be depolymerized by heating. The preirradiated polyacetal is placed in a sterilant package.

All the above described methods of generating a gaseous sterilant or disinfectant, with the exception of the '489 patent, involve generation of the sterilant gas by means of heat. As was noted above, heat is not suitable for all sterilization applications. Consequently, there is a need for novel sterilization systems and techniques which reduce or eliminate the disadvantages described above.

SUMMARY OF THE INVENTION

The present invention provides novel sterilants and methods of sterilization for use in disinfection and/or sterilization of objects. In one aspect a method of producing a sterilant involves providing a sterilant gas producing substrate and exposing the substrate to an effective gas releasing amount of ionizing radiation. Another aspect provides a method of sterilization wherein an object to be sterilized is contacted with a sterilant which comprises a combination of ionizing radiation and a sterilizing gas generated by irradiating a sterilant gas releasing substrate with ionizing radiation. In another aspect a sterilant comprises ionizing radiation in combination with a reaction product of a sterilant gas releasing substrate and ionizing radiation. In yet another aspect of the present invention a sterilizing device is provided which comprises means for producing ionizing radiation and an enclosure containing a sterilant gas releasing substrate. In still yet another aspect of the present invention a package for in situ sterilization of objects comprises a sealable pouch containing a sterilant gas releasing substrate capable of releasing sterilant gas upon exposure to ionizing radiation. A further aspect of the present invention provides an article sterilized by contacting the article with a sterilant which comprises a combination of ionizing radiation and a sterilizing gas generated by irradiating a sterilant gas releasing substrate with ionizing radiation. Any of the above-mentioned aspects may optionally incorporate a substance which absorbs the sterilant gas.

DETAILED DESCRIPTION OF THE INVENTION

According to the present invention a sterilant gas releasing substrate is subjected to an amount of ionizing radiation which is effective to cause at least partial vaporization of the substrate and the subsequent release of gas sterilant. The gas sterilant contacts the object to be sterilized to effect sterilization and/or disinfection.

The substrate may be liquid or solid. Suitable substrates include compositions derived from aldehydes, peroxides, oxides, aliphatic cyclic ethers, metal carbonyls, and halogens. Liquid substrates include peroxides and hydroperoxides. Solid substrates are useful when a liquid substrate would have a degradative effect on the object to be sterilized. Especially preferred are formaldehyde gas releasing solid substrates.

The following compounds are suitable formaldehyde releasing agents: oxymethylene based compositions such as paraformaldehyde, trioxymethylene, melamine formaldehyde, urea formaldehyde, phenol formaldehyde, and hexamethylenetetramine. In one embodiment, a solid copolymer of ethylene oxide and formaldehyde (sold commercially as Celcon TM) is used in accordance with the present invention to release a predominant amount of formaldehyde gas. The amount of formaldehyde in the copolymer may range from about 85% to about 99.9% by weight, and preferably from about 95% to about 99.9% by weight formaldehyde. In another embodiment a copolymer of trioxane and other cyclic ethers, such as 1,3-dioxolane and an alkylene formal is used in accordance with the present invention to release a predominant amount of formaldehyde gas. Suitable trioxane/cyclic ether copolymers contain at least about 85% by weight trioxane. Suitable alkylene formals include ethylene formal, propylene formal, and tetramethylene formal, with tetramethylene formal being preferred.

The above-mentioned solid substrates may be in powder form or may be shaped or otherwise molded into a film, mesh, filament, fabric or any other suitable shape depending on the application and the container in which sterilization is to occur. In one embodiment, a film or coating of the substrate is applied to a surface on or in the package containing an object or article to be sterilized.

To release sterilant gas from an above-described substrate, the substrate is subjected to an effective amount of ionizing radiation. Ionizing radiations include gamma rays, x-rays and electron beams. A preferred ionizing radiation according to the present invention is gamma radiation which is commonly produced from cobalt 60. Exposure of the substrates to gamma radiation causes the substrates to release sterilant gas. In the case of the polymeric substrates, radiolytic depolymerization occurs with consequent gas release.

As was mentioned above, gamma radiation can be used by itself and functions as both a volume and a surface sterilant. The traditional sterilization dose for industrial uses is about 2.5 megarads (Mrad). The Association for the Advancement of Medical Instrumentation (AAMI) has established guidelines for sterility assurance and recommends a $10^{-6}$ probability of surviving organisms. This is equivalent to one organism surviving on one million sterilized items. In most sterilization techniques the logarithm of the quantity of surviving organisms when plotted against the amount of absorbed radiation shows a linear relationship. The slope of the line is designated as K. The reciprocal of K gives the decimal reduction time, D. In order to quantify the rate at which microorganisms are killed the D value may be expressed kinetically. When plotted on logarithmic paper the kinetic death rates can be expressed in terms of D values which is the time required to destroy 90 percent of the bacterial cells or spore population under a given set of conditions. In food the most severe constraint for sterilization is equivalent to a 12D requirement (to sterilize C. Botulin) which means that if a given dose reduces an organism by one logarithmic cycle, then the material should be exposed to the equivalent of 12D values for sterilization. In the sterilization of medical materials the accepted D value for sterilization is 6D in the United State, Europe, and Australia.

In order to reach a D value of 6D, an exposure equivalent to at least about 2.5 Mrad (mega-rads) is required. Even though the accepted dose has been established at about 2.5 Mrad for sterilization, the actual dose can be lower based on the microbial flora routinely found on the product as well as to the products end use. An example of this is the establishment of a dose of about 2.0 Mrad for certain items being sterilized in a specific sterilization facility. See Herring, Radiation Sterilization at American Hospital Supply Corporation, Radiation Physical Chemistry, Vol. 14, pp. 55–59 (1979). The approved biological indicator for evaluating gamma sterilization is *Bacillus pumilus* in spore form. This organism is used due to its resistance to gamma radiation. The spores have an established D value of 0.15 Mrad which applies to spores on filter paper. When evaluating spore strips for growth and viability, sterile conditions should be maintained. Failure to maintain sterility can result in contamination of the cultures with consequent inaccurate results.

As was discussed above, the established sterilizing levels of ionizing radiation can have detrimental effects on polymeric materials and established effective levels of chemical gas sterilants are associated with other hazards. In accordance with the present invention, there is a combination effect between ionizing radiation and sterilant gas so that subthreshold levels of both may be used to achieve complete sterilization. Thus, low levels of ionizing radiation which do not adversely effect materials that would normally be degraded are used with less dangerous low levels of gas sterilant.

Examples of the polymeric devices or components of biomedical instruments or devices which are not usually recommended for high energy radiation sterilization at the doses of 2.5 to 3.5 Mrad due to undesirable radiation-induced degradation are those made of (a) non-absorbable thermoplastics such as polypropylene and polymethylpentene; (b) non-absorbable elastoplastics and thermoplastic elastomers made primarily of segmented polyether-esters, polyether-urethanes, and polyether-amides; (c) non-absorbable thermoplastic elastomers made primarily of polydienes (or hydrogenerated polydienes) and polystyrene block copolymers; (d) polyethylene devoid of any anti-oxidant/radiostabilizer and particularly the fugitive toxic types; and (e) polyether-esters and polyesters.

In accordance with the present invention, radiation doses as low as about 0.1 Mrads to about 2.3 Mrads or greater are effective when combined with gas sterilants to achieve effective sterilization. In one embodiment, an effective gas releasing amount of ionizing radiation is from about 0.7 mrad to about 1.4 Mrad. The amount of the generated gas sterilant is controlled linearly by the weight of the substrate and the radiation dose. The amount of gas sterilant is based on the volume contained within the sterilization chamber. The amount of gas sterilant released is proportional to the amount of substrate, i.e., increasing amounts of substrate contained in a chamber or other package allows for increasing volume of generated gas sterilant and a reduction of the radiation dose. Thus, the present invention allows nominal levels of radiation which contributes to the assured sterility of the objects and also induces the generation of gas sterilant from a suitable substrate to augment the radiosterilization process.

In one embodiment a solid substrate is shaped and configured to fit as a package insert. This allows in situ sterilization of packaged objects. For example, surgical sutures are sealed in packages prior to commercial release. A solid polymeric substrate such as polyoxymethylene or a copolymer of ethylene oxide and formaldehyde can be placed into the package which is then subsequently irradiated with gamma radiation to release the gas sterilant and completely sterilize the package interior and its contents. The sterilization environment may include any known media such as air, nitrogen, argon, etc.

Examples of articles used in medicine which can be sterilized in accordance with the present invention without incurring unacceptable loss of properties include: (a) absorbable sutures and particularly those containing the genetic glycolate, lactate, oxalate, carbonate, hydroxycaproate, hydroxyvalerate and/or hydroxybutyrate sequences; (b) non-absorbable sutures such as those made of polypropylene; (c) syringes and particularly those made of polypropylene; (d) ocular devices made primarily of silicones or methacrylate polymers; (e) mechanical ligating devices containing absorbable and/or non-absorbable components similar in chemical structure to those of the sutures described in items a & b; and (d) vascular grafts and surgical meshes containing absorbable and/or non absorbable components based on polymers of the chemical structures noted in items a & b. Other products made of any biocompatible material which can be sterilized according to the present invention include orthopedic pins, clamps, screws and plates, clips (e.g., for vena cava), staples, hooks, buttons and snaps, bone substitutes (e.g., mandible prosthesis), needles, non-permanent intrauterine devices, temporary draining or testing tubes or capillaries, surgical instruments, vascular implants or supports, vertebral discs, extracorporeal tubing for kidney and heart-lung machines, fibrillar products, knitted or woven, velours including burn dressings, hernia patches, absorbent paper or swabs, medicated dressings, facial substitutes, gauze, fabric, sheet, felt or sponge, dental packs, flake or powder for burns or abrasions, absorbable foam prosthesis, film for prosthetic devices, solid products which are molded or machined, reinforced bone pins, screws, etc., arterial graft or substitutes, bandages for skin surfaces, and burn dressings (in combination with other polymeric films).

Other examples of useful and unique applications of radiochemical sterilization according to the present invention include sterilization of surgical gowns, surgical gloves, large, complex surgical and operating room instruments, and red-bag waste, consisting primarily of disposable contaminated surgical devices and auxiliary equipment, which can be contaminated with tainted blood and biological fluids. A typical illustration of the later applications entails the use of mechanically sealable plastic bags containing polymeric inserts capable of the radiolyric release of the chemical adjuvant for radiochemical sterilization of the biologically harmful contents prior to solid waste disposal. Alternatively, liquid substrates can be sprayed or otherwise contacted with the above-mentioned medical supplies or wastes which are scaled in containers and then irradiated with ionizing radiation according to the present invention.

The sterilant gases generated in accordance with the present invention may optionally be removed by a sterilant gas absorbing substance. Gas absorbing substances are known in the art. Some examples include activated carbon, reactive polyamides, ion exchange resins such as Amberlite TM, certain citric acid based products which form a polysaccharide matrix on contact with formaldehyde gas such as Spill-X-S TM, (commercially available from Ansul Fire and Protection, Wisconsin), and polyhydric water soluble polymers disclosed in U.S. Pat. No. 4,374,814 incorporated herein by reference. The sterilant gas absorbing substances may be included, as package inserts, in packages or containers which are subjected to radiochemical sterilization according to the present invention.

The following examples help illustrate certain aspects of the present invention. These examples are illustrative and should not be construed to limit the present invention in any manner whatsoever.

EXAMPLE 1

Confirmation of *Bacillus Pumilus* Concentration 0.1 ml of the $3.4 \times 10^{10}$ CFU/ml concentration of *B. pumilus* ATCC 27142 (Raven Biological Laboratories, Omaha, Neb.) was added to 9.9 ml of sterile peptone broth for a $10^{-2}$ dilution. Three more 1/100 dilutions and a final 1/10 dilution were made. The dilutions of $10^{-8}$ and $10^{-9}$ were plated using the spiral plater method (Spiral Systems, Bethesda, Md.; Speck 1984). Another 0.1 ml amount of the *B. pumilus* culture was added to 9.9 ml of peptone and heated at 70° C. for 15 mixtures to heat shock the spores. The sample was then diluted and plated in the same manner as the first on trypticase soy agar TSA;BBL Microbiology Systems, Cokeysville, Md.).

| Normal conditions | Heat shocked |
|---|---|
| $4.4 \times 10^{10}$ CFU/ml | $2.4 \times 10^{10}$ CFU/ml |

It can be concluded that the stated concentration of $3.4 \times 10^{10}$ CFU/ml is accurate because the values obtained by this experiment were not significantly different. The experiment also shows that the spores do not have to be heat shocked to obtain a count of viable cells.

EXAMPLE 2

Preparation of Spore Strips and Vacutainer TM Tubes

Spore strips were prepared using aseptic technique under a sterile hood. 0.1 ml of the *B. pumilus* $3.4 \times 10^{10}$ CFU/ml suspension was added to each strip using an Eppendorf pipette and sterile tips. The strips were placed in sterile Vacutainer TM tubes (Terumo Medical Corporation, Elkton, Md.) using sterile forceps and the rubber stoppers were replaced. Twelve tubes were prepared in total. The tube contents are indicated as follows:

| Tube #1 | Subtilis Spore Strip |
|---|---|
| Tube #2 | Stearothermophilus Spore Strip |
| Tube #3 | 10.0 mg of Celcon M-90 |
| Tube #4 | 100.0 mg of Celcon M-90 |
| Tube #5 | 500.0 mg of Celcon M-90 |
| Tube #6 | Control Pumilis |
| Tube #11 | Subtilis Spore Strip |
| Tube #12 | Stearothermophilus Spore Strip |
| Tube #13 | 10.0 mg of Celcon M-90 |
| Tube #14 | 100.0 mg of Celcon M-90 |
| Tube #15 | 500.0 mg of Celcon M-90 |
| Tube #16 | Control Pumilis |

Each tube that contained Celcon M-90 (unstablized), had it placed at the bottom. Glass wool was placed above the Celcon M-90 (unstablized) but below the spore strip.

EXAMPLE 3

Gamma Irradiation, Incubation and Results (I)

Gamma radiation was obtained from a cobalt 60 source. Tubes 1–6 were exposed to 0.69 Mrad gamma radiation. Tubes 11–16 were exposed to 1.35 Mrad gamma radiation.

After about 20 hours in the irradiated tubes, the spore strips were aseptically removed from each tube and each strip was added to a 10 ml tube of trypticase soy broth (TSB). Control strips containing *B. stearothermophilus* and *B. subtilis*(Raven Biological Laboratories, Omaha, Neb.) were also added to TSB tubes. All of the tubes were incubated at 37° C. until positive growth was observed.

After 24 hours there was no visible growth. After 72 hours samples 2, 3, 4, 6, 13, and 16 were positive. The samples were diluted 1/100 and were plated using the spiral plater method to confirm that the turbidity was due to *B. pumilus*.

The plates were incubated at 37° C. for 24 hours. All of the plates had heavy growth and were pure cultures.

The remaining samples were incubated in the tubes for an additional 24 hours. After this time sample 5 showed turbidity while the others remained clear. All of the remaining samples were plated using the spiral plater method to check for any growth that was not visible. Samples 1, 11, 12, 14, and 15 were negative. Sample 5 had growth but not in as high of concentration as the previous positive samples (visual estimation). The tests results are summarized in Table I.

TABLE I

Spore Growth After Exposure to 0.69 and 1.35 Mrad Radiation

| Sample Number | 0.69 Mrad Contents | Growth 72 hours |
|---|---|---|
| 1 | *B. subtilis* | neg. |
| 2 | *B. stearothermophilus* | pos. |
| 3 | 10 mg Celcon M-90 | pos. |
| 4 | 100 mg | pos. |
| 5 | 500 mg | pos. (96 hours) |
| 6 | *B. pumilus* | pos. |

| Sample Number | 1.35 Mrad Contents | Growth 72 hours |
|---|---|---|
| 11 | *B. subtilis* | neg. |
| 12 | *B. stearothermophilus* | neg. |
| 13 | 10 mg | pos. |
| 14 | 100 mg | neg. |
| 15 | 500 mg | neg. |
| 16 | *B. pumilus* | pos. |

EXAMPLE 4

Tube Preparation, Gamma Irradiation, INCUBATION AND RESULTS (II)

Ten Vacutainer ™ tubes were prepared in a manner similar to Example 2, but all tubes contained *B. pumilus* with varying concentrations of Celcon M-90 (unstabilized), commercially available from Hoechst Celanese, as shown below:

| | |
|---|---|
| Tube No. 1 | 10 mg |
| Tube No. 2 | 20 mg |
| Tube No. 3 | 30 mg |
| Tube No. 4 | 40 mg |
| Tube No. 5 | 50 mg |
| Tube No. 6 | 60 mg |
| Tube No. 7 | 70 mg |
| Tube No. 8 | 80 mg |
| Tube No. 9 | 90 mg |
| Tube No. 10 | 100 mg |

The tubes were exposed to a total dose of 1.42 Mrad. The samples were plated using the spiral plater method and TSA plates. Samples 1 and 4 were positive and showed a high colony count. Samples 3, 8, 9, and 10 all contained one colony. The plates containing samples 2, 5, 6, 7, 8, 9, and 10 were pour plated by adding 1 ml of the trypticase soy broth to brain heart infusion agar. The plates were incubated at 37° C. overnight. All of the samples (2, 3, 5, 6, 7, 8, 9, 10) were negative. Since these results contradict the spiral plater results, the remaining media along with the spore strips were pour plated in trypticase soy agar. The plates were incubated at 37° C. overnight. All of the samples were negative. The results are summarized in Table II.

TABLE II

Spore Growth After Exposure to 1.42 Mrad Radiation

| Sample Number | Contents | Spiral Plate Count | Pour Plate Count |
|---|---|---|---|
| 1 | 10 mg Celcon M-90 | $7.8 \times 10^9$ CFU | — |
| 2 | 20 mg | neg. | neg. |
| 3 | 30 mg | 1 CFU | neg. |
| 4 | 40 mg | $6.0 \times 10^9$ CFU | — |
| 5 | 50 mg | neg. | neg. |
| 6 | 60 mg | neg. | neg. |
| 7 | 70 mg | neg. | neg. |
| 8 | 80 mg | 1 CFU | neg. |
| 9 | 90 mg | 1 CFU | neg. |
| 10 | 100 mg | 1 CFU | neg. |

EXAMPLE 5

Tube Preparation, Gamma Irradiation, Incubation and Results (III)

Forty-one tubes were prepared in a manner similar to Examples 2 and 4, having bacteria and the amounts of Celcon M-90 (unstablized), indicated below:

| Tube Nos. | Contents |
|---|---|
| 1, 21, 31, 41, 51 | *B. subtilis* |
| 2, 22, 32, 42, 52 | *B. stearothermophilus* |
| 3, 23, 33, 43, 53 | *B. pumilus* |
| 4, 24, 34, 44 | 50 mg Celcon M-90 |
| 5, 25, 35, 45 | 100 mg |
| 6, 26, 36, 46 | 200 mg |
| 7, 27, 37, 47 | 300 mg |
| 8, 28, 38, 48 | 400 mg |
| 9, 29, 39, 49, 54 | 500 mg |
| 55 | 10 mg |

Samples 51–55 were not exposed to gamma radiation to observe any effects caused by Celcon M-90 (unstablized) alone. The total dose for each set was:

| Tube Nos. | Radiation (approximate) |
|---|---|
| 1–9 | 0.50 Mrad |
| 21–29 | 0.75 Mrad |
| 31–39 | 1.00 Mrad |
| 41–49 | 1.25 Mrad |
| 51–55 | 0.00 Mrad |

The results are summarized below in Tables III–VI.

TABLE III

Spore Growth After Exposure to ≈0.50 Mrad Radiation

| Sample Number | ≈0.50 Mrad Contents | Growth 72 Hours |
|---|---|---|
| 1 | B. subtilis | $2.3 \times 10^6$ |
| 2 | B. stearothermophilus | neg. |
| 3 | B. pumilus | $1.8 \times 10^6$ |
| 4 | 50 mg | neg. |
| 5 | 100 mg | neg. |
| 6 | 200 mg | neg. |
| 7 | 300 mg | neg. |
| 8 | 400 mg | neg. |
| 9 | 500 mg | neg. |

TABLE IV

Spore Growth After Exposure to ≈0.75 Mrad Radiation

| Sample Number | Contents | Growth 72 Hours |
|---|---|---|
| 21 | B. subtilis | $2.2 \times 10^5$ |
| 22 | B. stearothermophilus | neg. |
| 23 | B. pumilus | $3.6 \times 10^6$ |
| 24 | 50 mg | neg. |
| 25 | 100 mg | neg. |
| 26 | 200 mg | neg. |
| 27 | 300 mg | neg. |
| 28 | 400 mg | neg. |
| 29 | 500 mg | neg. |

TABLE V

Spore Growth After Exposure to ≈1.00 Mrad Radiation

| Sample Number | ≈1.00 Mrad Contents | Growth 72 Hours |
|---|---|---|
| 31 | B. subtilis | neg |
| 32 | B. stearothermophilus | neg. |
| 33 | B. pumilus | neg. |
| 34 | 50 mg | $7.8 \times 10^5$ |
| 35 | 100 mg | neg. |
| 36 | 200 mg | neg. |
| 37 | 300 mg | neg. |
| 38 | 400 mg | neg. |
| 39 | 500 mg | $3.2 \times 10^5$ |

TABLE VI

Spore Growth After Exposure to ≈1.50 Mrad Radiation

| Sample Number | ≈1.50 Mrad Contents | Growth 72 Hours |
|---|---|---|
| 41 | B. subtilis | neg |
| 42 | B. stearothermophilus | neg. |
| 43 | B. pumilus | neg. |
| 44 | 50 mg | neg. |
| 45 | 100 mg | neg. |
| 46 | 200 mg | neg. |
| 47 | 300 mg | neg. |
| 48 | 400 mg | $1.1 \times 10^4$ |
| 49 | 500 mg | neg. |

The results from Example 3 indicate that a 0.69Mrad total dose was not high enough to cause complete sterilization. However, at 1.35Mrad, the samples containing 100 and 500 mg of Celcon M-90 (unstabilized) were negative. This is encouraging because according to the D value, it should take 2.25Mrad to bring the initial B. pumilus population of $3.4 \times 10^{10}$ to a $10^{-6}$ sterility level. The test in Example 4 produced similar results in Table II. The total dose was 1.42Mrad. This combined with 50mg of the Celcon M-90 (unstablized) achieved sterilization. Again, this level of radiation is much lower than the approximately 2.5Mrad necessitated by current standards. The results from Example 5 clearly show that Celcon M-90 (unstablized) is effective in combination with low doses of gamma radiation. Samples 51–55, which were not exposed to radiation, suffered no adverse effect from being in contact with the Celcon M-90 (unstablized). This indicates that the substrate is relatively stable until activated by ionizing radiation. Although samples 34, 39 and 48 showed some levels of growth, such growth could be from contamination or another speculative factor. The overall analysis of the results clearly indicates the efficacy of radiochemical sterilization according to the present invention.

EXAMPLE 6

Tube Preparation, Gamma Irradiation and Results (IV)

Thirteen tubes were prepared as follows. Celcon M-90 (unstablized) was cut and weighed to the below specified amounts and then placed in Vacutainer TM tubes. Certain of the tubes were inoculated with 0. ml of B. pumilus, B. subfilis and B. stearothermophilus. Tubes which contained just the spore strips were not separated by glass wool. Tubes containing Amberlite TM ion exchange resin had the Amberlite at the bottom, then a glass wool plug, the spore strips and film in successive layers. The tubes were tested in duplicate at 0.61 Mrads and 1.28 Mrads. The strips were removed aseptically and placed in tubes containing 10ml of brain heart infusion medium. The tubes were incubated for 6 days at 37° C. The tubes containing B. stearothermophilus were incubated at 55° C. for 6 days. The tubes were then inspected visually for growth. The results are summarized below in Table VII.

TABLE VII

Exposure of spore strips to 0.61 to 1.28 Mrads

| | 0.61 Mrads | | 1.28 Mrads | |
|---|---|---|---|---|
| Contents | Set 1 | Set 2 | Set 1 | Set 2 |
| Bacillus stearothermophilus | neg. | neg. | neg. | neg. |
| Bacillus pumilus | pos. | pos. | neg. | neg. |
| Bacillus subtilis | neg. | neg. | neg. | neg. |
| 50 mg Celcon M90 | neg. | neg. | neg. | neg. |
| 50 mg Celcon M90 + 150 mg Amberlite | neg. | neg. | neg. | neg. |
| 100 mg Celcon M90 | neg. | neg. | neg. | neg. |
| 100 mg Celcon M90 + 300 mg Amberlite | neg. | neg. | neg. | neg. |
| 200 mg Celcon M90 | neg. | neg. | neg. | neg. |
| 200 mg Celcon M90 + 600 mg Amberlite | neg. | neg. | neg. | neg. |
| 300 mg Celcon M90 | neg. | neg. | neg. | neg. |
| 300 mg Celcon M90 + 900 mg Amberlite | neg. | neg. | neg. | neg. |
| 400 mg Celcon M90 | neg. | neg. | neg. | neg. |
| 400 mg Celcon M90 + 900 mg Amberlite | neg. | neg. | neg. | neg. |

Both levels of irradiation were effective in killing all of the samples of Example 6 except in the 0.61 Mrad irradiation of the pure B. pumilus. This can be explained by the fact that B. pumilus is used as an indicator for the effectiveness of gamma irradiation and about 2.5 Mrads is the recommended dose for a 100% kill. The fact that the other samples contained the same B. pumilus culture and were irradiated at the same level of 0.61 Mrads, yet still were negative, indicates that the presence of the Celcon M-90 (unstablized) is contributing to the sterilization process.

The principles, preferred embodiments and modes of operation of the invention have been described in the foregoing specification. The invention which is intended to be protected herein, however, is not to be construed as limited to the particular forms disclosed, since they are to be regarded as illustrative rather than restrictive. Modifications and variations of the present invention are possible in light of the above teachings. It is therefore to be understood that changes may be made in particular embodiments of the invention described which are within the full intended scope of the invention as defined by the following claims.

What is claimed is:

1. A method of producing a sterilant comprising providing a sterilant gas releasing substrate and exposing said substrate to an effective gas releasing amount of ionizing radiation which depolymerizes said sterilant gas releasing substrate and releases a sterilant gas.

2. A method of producing a sterilant according to claim 1 wherein said substrate comprises a solid sterilant gas releasing substrate.

3. A method of producing a sterilant according to claim 1 wherein said substrate comprises a liquid sterilant gas releasing substrate.

4. A method of producing a sterilant according to 1 wherein said substrate comprises a formaldehyde gas releasing substrate.

5. A method of producing a sterilant according to claim 4 wherein said substrate is selected from the group consisting of paraformaldehyde, polyoxymethylene, melamine-formaldehyde, urea-formaldehyde, phenol-formaldehyde, hexamethylenetetramine, copolymers of ethylene oxide and formaldehyde, and copolymers of trioxane and a member selected from the group consisting of 1,3 dioxolane and an alkylene formal.

6. A method of producing a sterilant according to claim 1 wherein gas released from said gas releasing substrate is formaldehyde.

7. A method of producing a sterilant according to claim 1 wherein said ionizing radiation is selected from the group consisting of gamma radiation, x-rays and electron beam radiation.

8. A method of producing a sterilant according to claim 7 wherein the effective gas releasing amount of ionizing radiation is from about 0.1 Mrad to about 2.3 Mrad.

9. A method of producing a sterilant according to claim 8 wherein the effective gas releasing amount of ionizing radiation is from about 0.7 Mrad to about 1.4 Mrad.

10. A method of producing a sterilant according to claim 2 wherein said solid sterilant gas releasing substrate is formed into a material selected from the group consisting of film, mesh, filament, fabric, coating and powder.

11. A method of sterilizing comprising contacting an object to be sterilized with a sterilant which comprises a combination of ionizing radiation and a sterilizing gas generated by irradiating and depolymerizing a sterilant gas releasing substrate with ionizing radiation.

12. A sterilant comprising ionizing radiation in combination with the reaction product of a sterilant gas releasing substrate, capable of depolymerizing on exposure to ionizing radiation and ionizing radiation.

13. A sterilant device comprising means for producing ionizing radiation and an enclosure containing a sterilant gas releasing substrate which depolymerizes on exposure to ionizing radiation and release a sterilant gas.

14. A package for in situ sterilization of articles comprising a sealable pouch containing a sterilant gas releasing substrate capable of depolymerizing and releasing sterilant gas upon exposure to ionizing radiation.

15. A package according to claim 14 further comprising a sterilant gas absorbing substance.

16. A package according to claim 15 wherein said sterilant gas absorbing substance is selected from the group consisting of activated carbon, citric acid based polysaccharide matrix materials, ion exchange resins and polyhydric water soluble polymers.

17. An article sterilized by contacting the article with a sterilant which comprises a combination of ionizing radiation and a sterilizing gas generated by irradiating and depolymerizing a sterilant gas releasing substrate with ionizing radiation.

18. An article according to claim 17 wherein said article is an article used in medicine.

19. An article according to claim 17 wherein said article used in medicine comprises a bioabsorbable material.

20. An article according to claim 17 wherein said article used in medicine comprises polypropylene.

21. A method of producing a sterilant according to claim 1 wherein an effective gas releasing amount of ionizing radiation is from about 0.5 to about 2.3 Mrad.

* * * * *